(12) United States Patent
Hill

(10) Patent No.: US 12,213,846 B2
(45) Date of Patent: Feb. 4, 2025

(54) APPARATUS AND METHOD TO INSPECT MICROLUMEN OF CATHETER

(71) Applicant: SterilMed, Inc., Plymouth, MN (US)

(72) Inventor: Jason Hill, Brooklyn Park, MN (US)

(73) Assignee: Sterilmed, Inc., Plymouth, MN (US)

( * ) Notice: Subject to any disclaimer, the term of this patent is extended or adjusted under 35 U.S.C. 154(b) by 584 days.

(21) Appl. No.: 17/406,141

(22) Filed: Aug. 19, 2021

(65) Prior Publication Data

US 2023/0056243 A1 Feb. 23, 2023

(51) Int. Cl.
| | |
|---|---|
| *A61B 90/70* | (2016.01) |
| *B08B 9/04* | (2006.01) |
| *G01N 7/00* | (2006.01) |
| *A61M 25/00* | (2006.01) |

(52) U.S. Cl.
CPC ............... *A61B 90/70* (2016.02); *B08B 9/04* (2013.01); *G01N 7/00* (2013.01); *A61B 2090/701* (2016.02); *A61B 2090/702* (2016.02); *A61M 2025/0019* (2013.01); *A61M 2205/0266* (2013.01); *A61M 2205/3317* (2013.01); *B08B 2209/04* (2013.01)

(58) Field of Classification Search
CPC .................................. B08B 9/04; A61B 90/70
See application file for complete search history.

(56) References Cited

U.S. PATENT DOCUMENTS

| | | | |
|---|---|---|---|
| 4,721,123 A * | 1/1988 | Cosentino | ............. A61M 25/10 134/57 R |
| 6,783,524 B2 | 8/2004 | Anderson et al. | |
| 7,752,684 B1 | 7/2010 | Pieretti | |
| 9,314,299 B2 | 4/2016 | Fang | |
| 9,907,480 B2 | 3/2018 | Basu et al. | |
| 10,702,177 B2 | 7/2020 | Aujla | |
| 10,830,682 B1 | 11/2020 | Fowler et al. | |
| 2004/0130332 A1 * | 7/2004 | Harris | ................... G01M 3/005 138/108 |
| 2009/0192354 A1 | 7/2009 | Hasegawa | |
| 2013/0018304 A1 | 1/2013 | Bagwell et al. | |
| 2017/0151035 A1 | 6/2017 | Nguyen et al. | |
| 2019/0336714 A1 | 11/2019 | Vazales et al. | |
| 2021/0170127 A1 | 6/2021 | Salinas et al. | |

OTHER PUBLICATIONS

Partial European Search Report dated Jan. 2, 2023, for Application No. 22190917.9, 13 pages.
Extended European Search Report dated Feb. 6, 2024, for Application No. 23210176.6, 7 pages.

* cited by examiner

*Primary Examiner* — Walter L Lindsay, Jr.
*Assistant Examiner* — Andrew V Do
(74) *Attorney, Agent, or Firm* — Frost Brown Todd LLP

(57) ABSTRACT

A lumen inspection device includes an elongate member and a sealing member at a distal end of the elongate member. The elongate member is inserted into a lumen of a medical instrument. The lumen inspection device is translated along the lumen. The sealing member resiliently bears against a sidewall of the lumen as the lumen inspection device is translated along the lumen of the medical instrument. A pressure source is activated to pressurize a region of the lumen adjacent to the sealing member. A fluid property of the lumen is monitored to detect whether the sealing member deforms in response to an obstruction in the lumen.

20 Claims, 10 Drawing Sheets

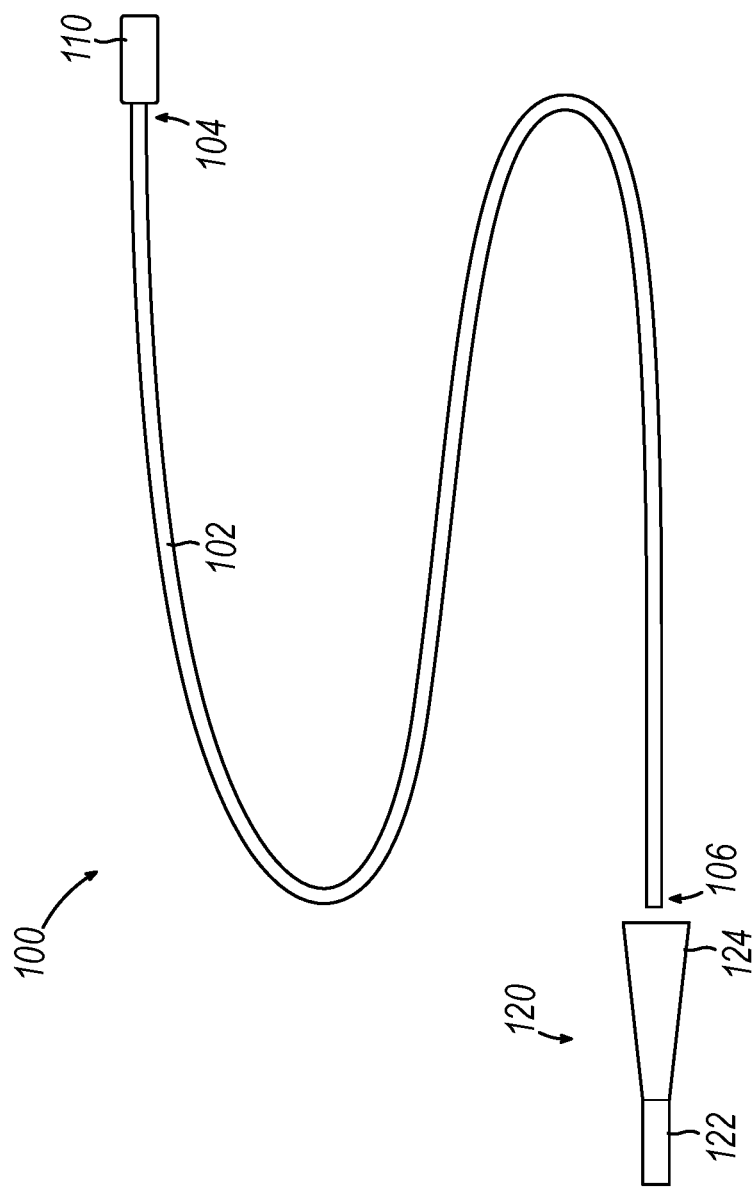

APPARATUS AND METHOD TO INSPECT MICROLUMEN OF CATHETER

BACKGROUND

Various medical instruments include lumens that extend along a substantial length (e.g., ranging from approximately 36 inches to approximately 60 inches) and have a substantially small diameter (e.g., ranging from approximately 0.010 inches to approximately 0.030 inches). This may include instruments such as catheters, dilators, endoscopes, and other kinds of instruments. In some scenarios, after a medical instrument is used in a first medical procedure (e.g., in a first patient), it may be desirable to clean and reprocess the medical instrument to enable the medical instrument to be safely used in a second medical procedure (e.g., in a second patient). If a contaminant is left in the lumen, the contaminant may cause harm to a patient in a subsequent medical procedure, particularly if the medical instrument is used in a cardiovascular system. Such safety concerns may be reflected in regulations that require cleaning and reprocessing procedures to achieve a certain degree of particle removal (e.g., regulations requiring that no particles having a size of 50 microns or larger be left in the lumen). When a medical instrument has a lumen with a substantial length and/or a substantially small diameter, it may be relatively difficult to sufficiently clean and otherwise reprocess the lumen to remove any contaminants therein.

After a medical instrument with a lumen having a substantial length and/or a substantially small diameter has been cleaned and otherwise reprocessed, it may be difficult to inspect the lumen to ensure that the cleaning process was successful. For instance, some methods may include insertion of a borescope into the lumen to visually inspect for contaminants in the lumen. In some cases, the image quality of the borescope may be unsatisfactory for visual detection of particles that are relatively small yet still exceed a size threshold that is established by regulations or that otherwise presents safety risks. When the medical instrument has a transparent sidewall defining the lumen, it may also be difficult to discern via visual inspection with a borescope whether particles are actually in the lumen or on the exterior of the sidewall.

Another method of inspecting lumens in cleaned or otherwise reprocessed medical instruments may include micro-CT scanning, where the medical instrument is scanned with x-rays to generate a 3D image. To the extent that this method facilitates detection of small particles in lumens of medical instruments, such a method may not be feasible in cases where the medical instrument includes radiopaque components (e.g., a stainless steel wire braid, pull-wires, coils, electrical wires, etc.) adjacent to the lumen.

Yet another method of inspecting lumens in cleaned or otherwise reprocessed medical instruments may include a mass air flow test, where air is flowed through the lumen. The presence of an occlusion (e.g., particle or other contaminant) in the lumen may reduce the mass flow as compared to the flow through an unobstructed lumen. The effectiveness of this method may vary based on the dimensions of the lumen, the size of the occlusion, and the longitudinal position at which the occlusion is located in the lumen. For instance, in a medical instrument having a lumen with a cross-sectional area of approximately $2.27 \times 10^{-4}$ in$^2$ and a length of approximately 56.25 inches, it may be possible to detect an occlusion having a diameter of approximately 50 microns near the proximal end of the lumen but not near the distal end of the lumen.

Yet another method of inspecting lumens in cleaned or otherwise reprocessed medical instruments may include particle counting. Such particle counting may be performed using a variety of techniques, including light obscuration to detect the number and size distribution of particles in a solution. However, this method may only be suitable for non-adherent particles.

Further examples of detecting particulates in lumens are described in U.S. Pat. No. 10,830,682, entitled "Test Method Development for Mass Flow Identification of Occluding Small Particulates in Microlumens," issued Nov. 10, 2020.

While a variety of devices and methods have been used to inspect and reprocess medical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3A depicts a schematic view of an example of a lumen inspection device, with a sealing member decoupled from a wire member;

Figure 1:
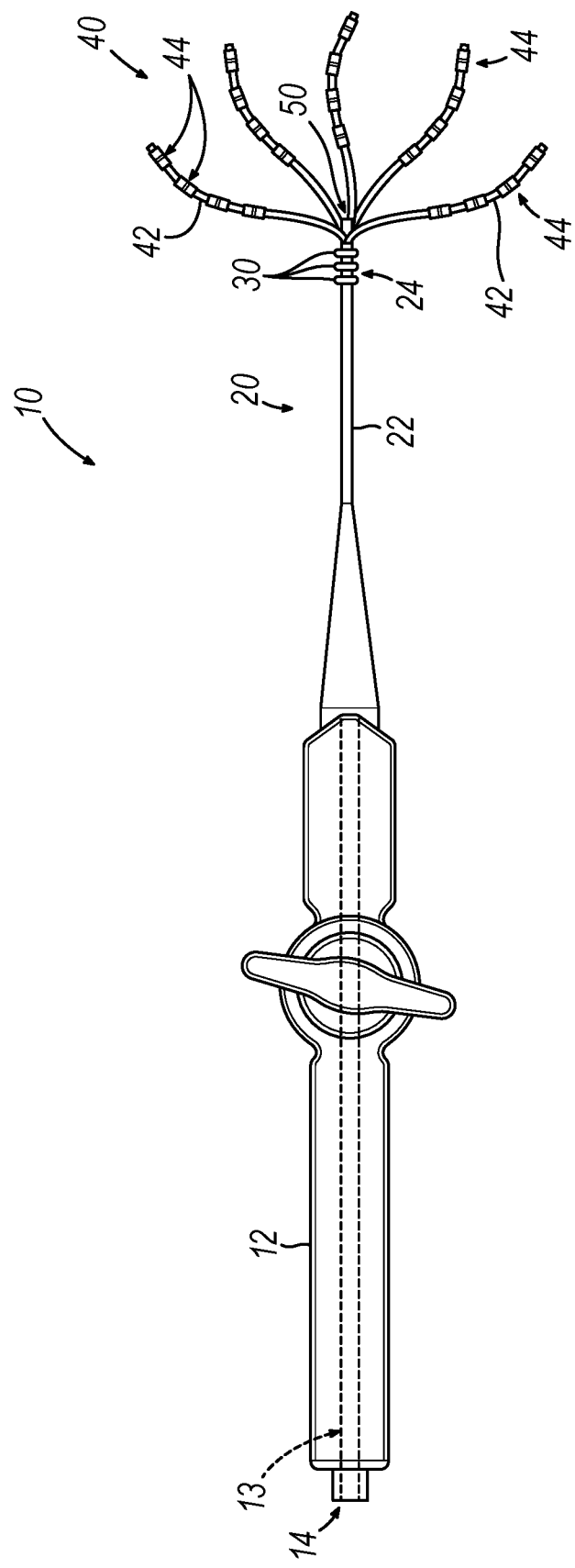
FIG. 1 depicts a schematic view of an example of a catheter instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Example of Catheter Instrument

FIG. 1 shows an example of a catheter instrument (10). Catheter instrument (10) of this example includes a handle (12), a shaft assembly (20) extending distally from handle (12), and an end effector (40) located at the distal end (24) of shaft assembly (20). A port (14) is located at the proximal end of handle (12). In some versions, port (14) includes one or more luer fittings. In addition, port (14) may include one or more fluid-tight seals. Shaft assembly (20) includes a catheter shaft (22) and a plurality of ring electrodes (30). As shown in FIGS. 5A-6C and as described in greater detail below, catheter shaft (22) defines a lumen (52) that distally terminates in a distal opening (50). Distal opening (50) is located adjacent to end effector (40). Lumen (52) is in communication with port (14) via a passageway (13) formed through handle (12).

Figure 2:
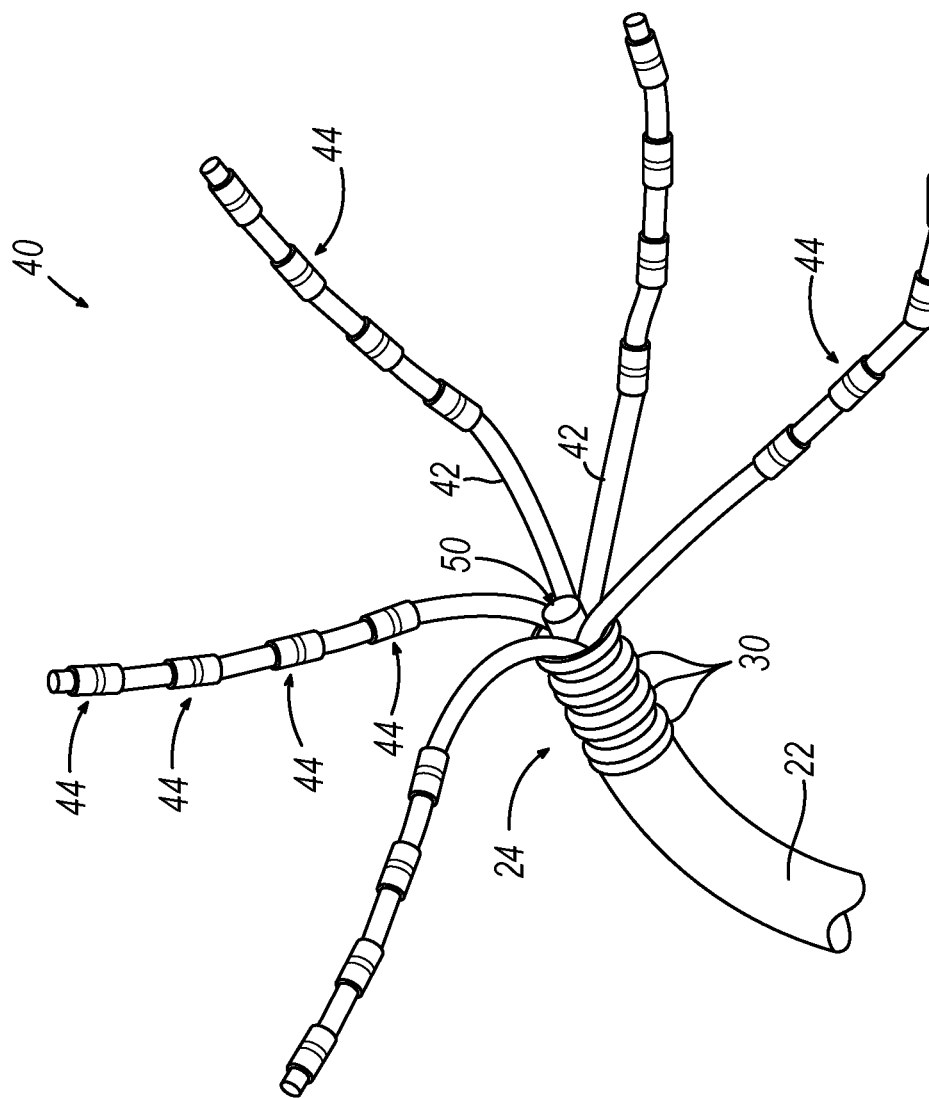
FIG. 2 depicts a perspective view of an end effector of the catheter instrument of FIG. 1.

FIG. 2 shows end effector (40) in greater detail. As shown, end effector (40) of this example includes a plurality of flexible arms (42). Each arm (42) includes several electrode pairs (44) spaced apart along the length of arm (42). In some versions, arms (42) are resiliently biased to splay outwardly; yet may also flex toward a central longitudinal axis defined by catheter shaft (22). Such inward flexing may enable end effector (40) to fit within a sheath (not shown) as end effector (40) is guided to a target site within a patient. Such a target site may include a pulmonary vein, a chamber of a heart, and/or another region of a cardiovascular system.

Ring electrodes (30) and electrode pairs (44) may be electrically coupled with a control module (not shown). Electrode pairs (44) may be used to pick up electrical potentials within a pulmonary vein, chambers of a heart, and/or other regions of a cardiovascular system to thereby map locations of aberrant electrical signals within such anatomical structures. During such a mapping process, ring electrodes (30) may be used to generate a reference signal (e.g., based on potentials picked up via the patient's blood). In addition, or in the alternative, electrode pairs (44) may be used to apply bipolar RF energy to tissue within cardiovascular anatomical structures, to thereby ablate the tissue as part of a treatment for atrial fibrillation, other kinds of arrhythmia, and/or other conditions. During a mapping process and/or during an ablation process, a source of irrigation fluid (e.g., saline) may be coupled with port (14); and the irrigation fluid may be communicated along passageway (13) and lumen (52), such that the irrigation fluid ultimately exits catheter instrument (10) via distal opening (50). Such irrigation fluid may prevent formation of coagulum at distal end (24) and at end effector (40).

In addition to the foregoing, catheter instrument (10) may be constructed and operable in accordance with at least some of the teachings of U.S. Pat. No. 9,314,299, entitled "Flower Catheter for Mapping and Ablating Veinous and Other Tubular Locations," issued Apr. 19, 2016, the disclosure of which is incorporated by reference herein in its entirety; U.S. Pat. No. 9,907,480, entitled "Catheter Spine Assembly with Closely-Spaced Bipole Microelectrodes," issued Mar. 6, 2018, the disclosure of which is incorporated by reference herein in its entirety; and/or U.S. Pat. No. 10,702,177, entitled "Catheter with Bipole Electrode Spacer and Related Methods," issued Jul. 7, 2020, the disclosure of which is incorporated by reference herein in its entirety.

II. Example of Lumen Inspection Device and Method

At any stage of the process of using an instrument like catheter instrument (10) in a first medical procedure in a patient, particles and/or other contaminants may enter lumen (52). Such particles and/or other contaminants may remain in lumen (52) even after catheter instrument (10) has been subject to processes to clean and/or otherwise process catheter instrument (10) after catheter instrument (10) has been used in the first medical procedure. It may be desirable to provide an apparatus and method that may be used to reliably determine whether a cleaning process has sufficiently removed particles and/or other contaminants from lumen (52) before catheter instrument (10) is used in a subsequent medical procedure. An example of such an apparatus and method is described in greater detail below. While the following example is provided in the context of catheter instrument (10), the below teachings may be readily applied to any other kind of instrument that has one or more lumens. By way of example only, the below teachings may be readily applied to catheters (e.g., with an irrigation lumen and/or a guidewire lumen, etc.), endoscopes, and dilators. Other suitable kinds of instruments to which the below teachings may be applied will be readily apparent to those skilled in the art in view of the teachings herein.

Figure 3B:
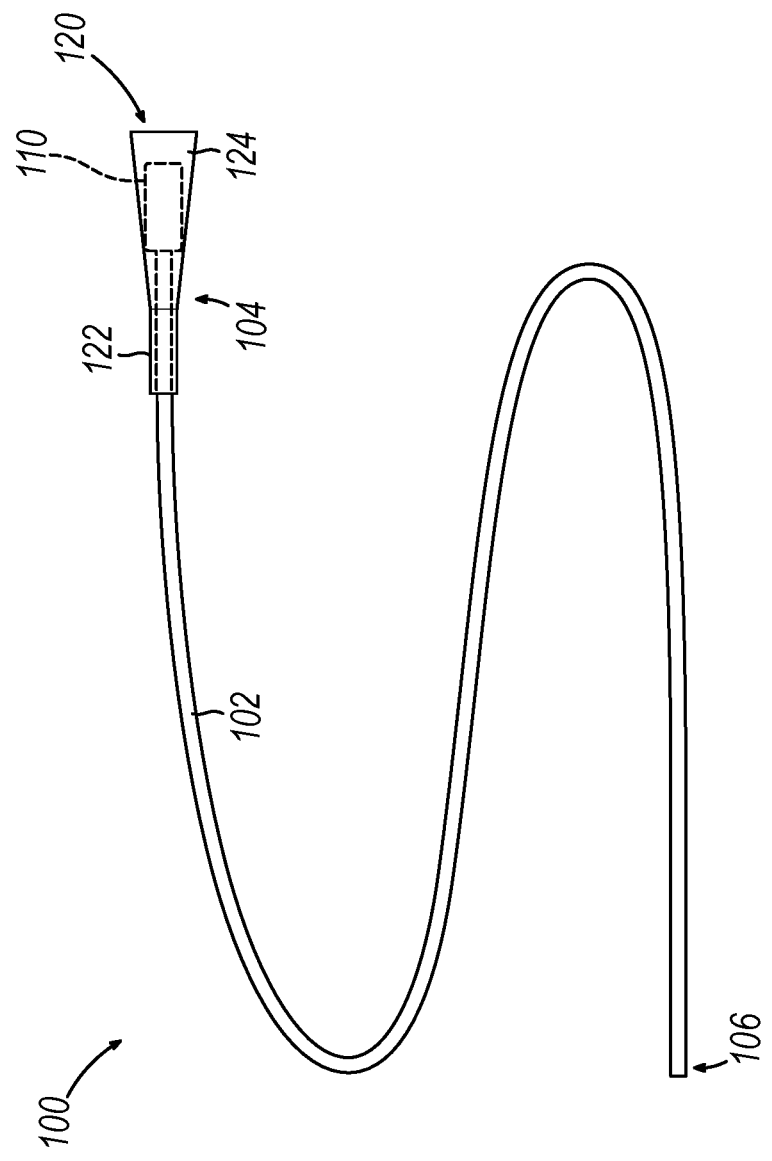
FIG. 3B depicts a schematic view of the lumen inspection device of FIG. 3A, with the sealing member disposed on the wire member.

FIGS. 3A-3B show an example of a lumen inspection device (100). Lumen inspection device (100) of this example includes a wire member (102) and a sealing member (120). Wire member (102) includes a distal end (104) and a proximal end (106), with a stop member (110) fixedly secured to distal end (104). In the present example, stop member (110) has a cylindraceous shape. Alternatively, stop member (110) may be frustoconical or have any other suitable shape. Wire member (102) is formed of a flexible material having a high degree of tensile strength, such that wire member (102) is not longitudinally extensible. Wire member (102) also provides a substantial resistance to kinking or buckling during use of lumen inspection device (100) as described in greater detail below. By way of example only, wire member (102) may be formed of metal, polymer, and/or any other suitable material or combination of materials. In some versions, wire member (102) comprises superelastic nitinol.

Sealing member (120) of the present example is generally frustoconical in shape and includes a sleeve portion (122) and a flared portion (124) extending distally from sleeve portion (122). Sealing member (120) is formed of a polymeric material that is resiliently biased to form a tapered profile along flared portion (124). By way of example only, flared portion (124) may have a modulus of elasticity ranging from approximately 2.2 GPa to approximately 3.2 GPa; or more particularly approximately 2.7 GPa. Any suitable material or combination of materials may be used to form sealing member (120). In the present example, sealing member (120) is formed of a material that is softer than the material forming sidewall of lumen (52). By way of example only, some versions of sealing member comprise polyethylene terephthalate (PET); while the material forming sidewall of lumen (52) comprises polyimide. By way of further example only, the material forming flared portion (124) may have a wall thickness ranging from approximately 0.00010 inches to approximately 0.00025 inches; or more particularly approximately 0.00018 inches. Such wall thickness may ensure that flared portion (124) provides an appropriate balance between sealing against the sidewall of lumen (52) and deforming in response to contaminants (54) as described in greater detail below. Sealing member (120) is configured such that the distal end of flared portion (124) has a diameter that is approximately equal to, or slightly larger than, the diameter of a lumen in which lumen inspection device (100) will be used.

As shown in FIGS. 3A-3B, lumen inspection device (100) may be assembled by inserting proximal end (106) of wire member (102) into flared portion (124) of sealing member (120), then sliding sealing member (120) distally along wire member (102) until sealing member (120) reaches distal end (104). In some versions, sealing member (120) is slid distally along wire member (102) while wire member (102) remains stationary. In some other versions, wire member (102) is pulled proximally relative to sealing member (120) while sealing member (120) remains stationary. In any case, once sealing member (120) reaches distal end (104) of wire member (102), stop member (110) may engage the interior region of flared portion (124) as shown in FIG. 3B; and thereby arrest further proximal movement of wire member (102) relative to sealing member (120).

With wire member (102) and sealing member (120) assembled together, sleeve portion (122) extends along part of distal end (104) of wire member (102). In some versions, sleeve portion (122) is bonded to the corresponding portion of wire member (102) and/or stop member (110) after reaching the state of assembly shown in FIG. 3B. By way of example only, an adhesive may be used to provide such bonding. By way of further example only, sleeve portion (122) may include a heat-shrink material, such that heat may be applied to sleeve portion to cause sleeve portion (122) to shrink around and thereby grip the corresponding portion of wire member (102) and/or stop member (110). Thus, sleeve portion (122) may be thermally bonded directly to wire member (102) and/or stop member (110). Any other suitable techniques may be used to bond sleeve portion (122) to wire member (102) and/or stop member (110). In addition to mechanically securing sleeve portion (122) to wire member (102) and/or stop member (110), such bonding may prevent air from leaking between sleeve portion (122) and wire member (102) and/or between sleeve portion (122) and stop member (110).

In some other variations, sleeve portion (122) is not bonded to wire member (102). In such versions, engagement between stop member (110) and flared portion (124) may keep sealing member (120) and wire member (102) sufficiently together as lumen inspection device (100) is pulled through lumen (52) as described in greater detail below. As yet another example, sealing member (120) and wire member (102) may be integrally formed together as a monolithic unit. Alternatively, lumen inspection device (100) may be formed in any other suitable fashion using any other suitable processes.

Figure 4A:
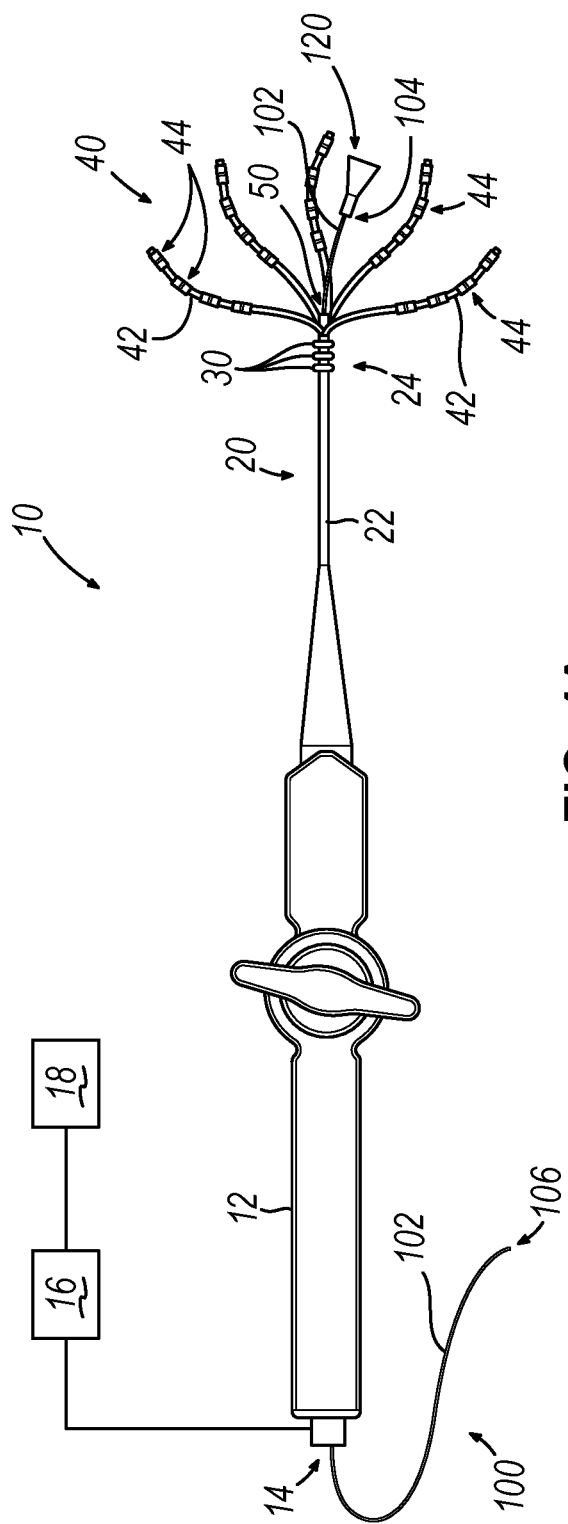
FIG. 4A depicts a schematic view of the lumen inspection device of FIG. 3A disposed in the catheter instrument of FIG. 1, with the sealing member positioned distally in relation to a lumen of the catheter instrument.
Figure 4B:
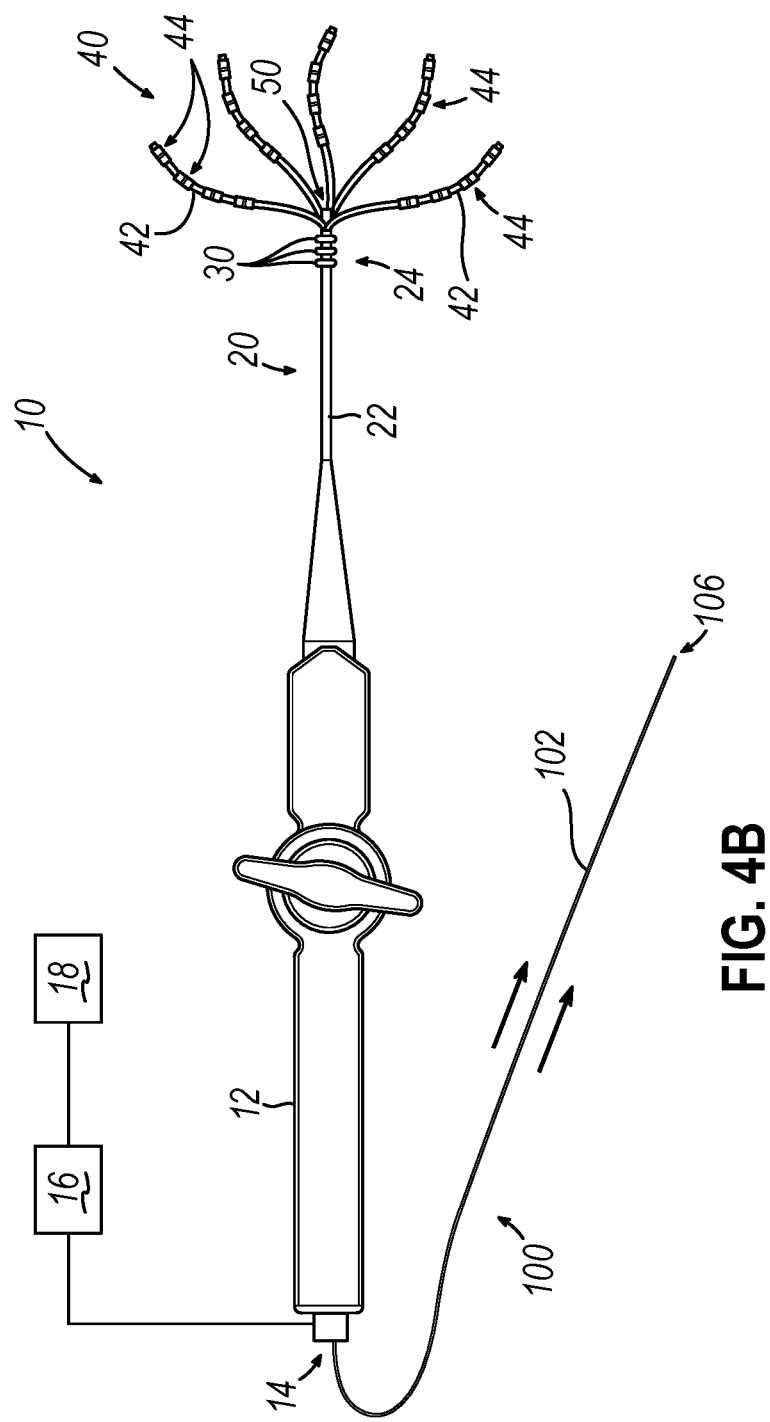
FIG. 4B depicts a schematic view of the lumen inspection device of FIG. 3A disposed in the catheter instrument of FIG. 1, with the sealing member positioned internally with in the lumen of the catheter instrument.

FIGS. 4A-4B show an example of how lumen inspection device (100) may be used with catheter instrument (10). As shown, in FIG. 4A, proximal end (106) of wire member (102) is inserted into lumen (52) via distal opening (50). Wire (102) is fed proximally along lumen (52) and passageway (13) until proximal end (106) exits handle (12) via port (14). At the stage shown in FIG. 4A, sealing member (120) has not yet entered distal opening (50) into lumen (52). As shown in FIG. 4B, the operator continues to pull wire member (102) such that sealing member (120) eventually enters lumen (52) via distal opening (50).

As also shown in FIGS. 4A-4B, a flow sensor (16) and pressure source (18) are coupled with port (14) during this procedure. Pressure source (18) is operable to communicate pressurized fluid (e.g., pressurized air) to lumen (52) via port (14) and passageway (13). Pressure source (18) may comprise a pump and/or any other suitable components. By way of example only, pressure source (18) may be configured to generate a fluid pressure of approximately 20 psi. Alternatively, any other suitable fluid pressure may be used.

Flow sensor (16) is operable to sense flow of fluid within lumen (52). Various suitable forms that flow sensor (16) may take will be apparent to those skilled in the art in view of the teachings herein. Port (14) is configured to provide a dynamic, fluid-tight fit about wire member (102). Thus, as lumen inspection device (100) is pulled proximally relative to catheter instrument (10), the pressurized fluid generated by pressure source (18) does not escape through the interface between port (14) and wire member (102). Due to the sealing fit between sealing member (120) and the inner sidewall of lumen (52), the region of lumen (52) that is proximal to sealing member (120) will remain at a fluid pressure established by pressure source (18) until sealing member (120) encounters a contaminant in lumen (52) as described in greater detail below.

Moreover, the pressurized fluid will not substantially flow past sealing member (120) as sealing member (120) maintains a sealed fit against the inner sidewall of lumen (52). Flow sensor (16) may operate continuously to detect any changes in the flow rate of fluid through lumen (52). In some cases, a nominal amount of pressurized fluid may flow from lumen (52), through the interface between sealing member (120) and the inner sidewall of lumen (52) and/or through the interface between wire member (102) and port (14); and flow sensor (16) may detect such nominal flow. By way of example only, this nominal fluid flow rate may range from approximately 0 standard cubic centimeters per minute (SCCM) to approximately 15 SCCM. The fluid flow rate may substantially increase (e.g., spike) in the event that sealing member (120) encounters a contaminant (54) as described below. As soon as sealing member (120) enters lumen (52) via distal opening (50) and pressure source (18) is activated, flow sensor (16) may be used to immediately take a baseline reading to determine the nominal flow rate of fluid through lumen (52).

FIGS. 5A-5C and 6A-6C show sealing member (120) traversing a region of lumen (52) that includes a contaminant (54) on the sidewall of lumen (52). By way of example only, contaminant (54) may include a particle, such as biological material, manmade material, etc., in the sidewall of lumen (52) even after catheter instrument (10) has been cleaned and reprocessed for use in a second medical procedure after being used in a first medical procedure. Contaminant (54) may be adhered to the sidewall of lumen (52) or may be loosely contained in lumen (52).

Figure 5A:
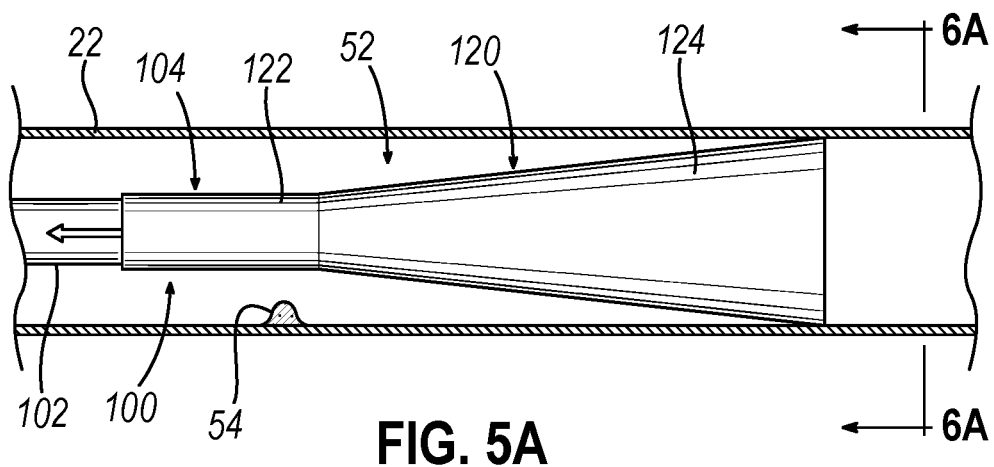
FIG. 5A depicts a cross-sectional side view of the lumen inspection device of FIG. 3A disposed in the catheter instrument of FIG. 1, with the sealing member positioned internally within the lumen of the catheter instrument, and with the sealing member positioned distally in relation to a particle in the lumen.
Figure 6A:
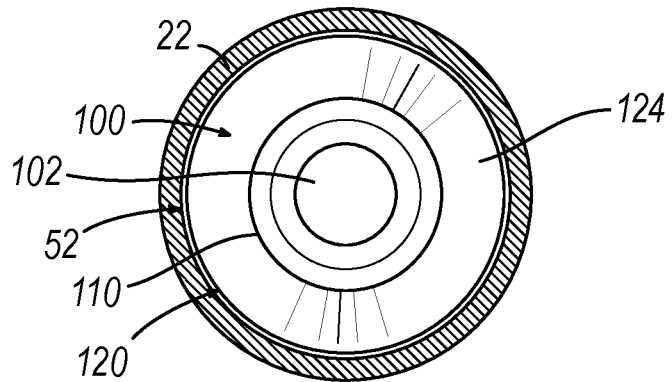
FIG. 6A depicts a cross-sectional end view of the lumen inspection device of FIG. 3A disposed in the catheter instrument of FIG. 1, taken along line 6A-6A of FIG. 5A.

At the stage shown in FIGS. 5A and 6A, sealing member (120) is positioned distally in relation to contaminant (54). At this stage, pressure source (18) maintains a substantially constant positive fluid pressure level in the region of lumen (52) proximal to sealing member (120). As noted above, sealing member (120) is resiliently biased to form a tapered profile along flared portion (124), such that sealing member (120) resiliently bears against the sidewall of lumen (52) to thereby provide a sealing fit along the sidewall of lumen (52). With sealing member (120) providing a sealing fit along the sidewall of lumen (52), sealing member (120) prevents the pressurized fluid from escaping lumen (52) distally past sealing member (120). A seal (not shown) in port (14) prevents the pressurized fluid from escaping through the interface between port (14) and wire member (102). The operator may continue to pull lumen inspection device (100) proximally through lumen (52), with flow sensor (16) tracking the rate of fluid flow through lumen (52), to ensure that the flow rate is at a zero value or a nominal value, to thereby ensure that sealing member (120) is appropriately sealed against the sidewall of lumen (52). It should also be noted that the resilience of sealing member (120) prevents the weight of wire member (102) and stop member (110) from causing sealing member (120) to collapse as lumen inspection device (100) traverses lumen (52). Flared portion (124) of sealing member (120) will thus maintain its frustoconical shape during transit along lumen, until sealing member (120) encounters a contaminant or other obstruction, etc., on the sidewall of lumen (52).

Figure 5B:
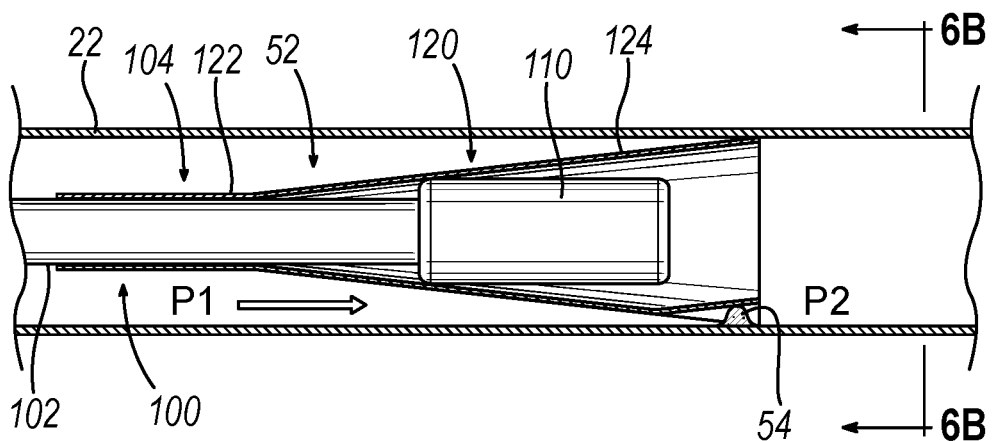
FIG. 5B depicts a cross-sectional side view of the lumen inspection device of FIG. 3A disposed in the catheter instrument of FIG. 1, with the sealing member positioned internally with in the lumen of the catheter instrument, and with the sealing member positioned to engage the particle in the lumen.
Figure 6B:
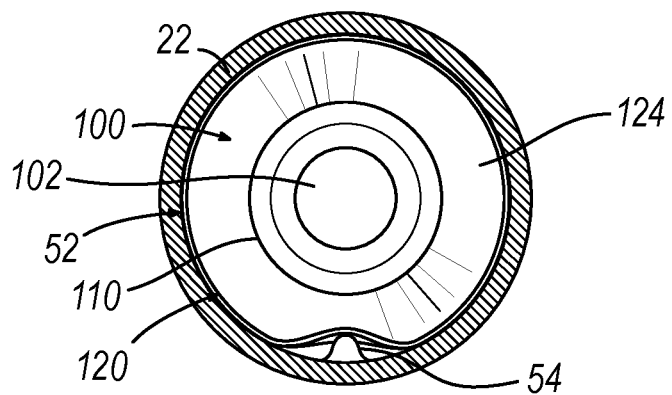
FIG. 6B depicts a cross-sectional end view of the lumen inspection device of FIG. 3A disposed in the catheter instrument of FIG. 1, taken along line 6B-6B of FIG. 5B.

At the stage shown in FIGS. 5B and 6B, sealing member (120) encounters contaminant (54). This causes a flared portion (124) to deform inwardly. This inward deformation of flared portion (124) effectively breaks the fluid seal between sealing member (120) and the sidewall of lumen (52). This break in the fluid seal allows pressurized fluid to pass from the region of lumen (52) proximal to sealing member (120) to the region of lumen (52) distal to sealing member, such that at least some pressurized fluid may ultimately escape via distal opening (50). The passage of pressurized fluid distally past sealing member (120) causes a sudden increase in the flow rate of fluid through lumen (52). This sudden increase in fluid flow rate is detected by flow sensor (16). The operator may continue to pull lumen inspection device (100) proximally through lumen (52).

Figure 5C:
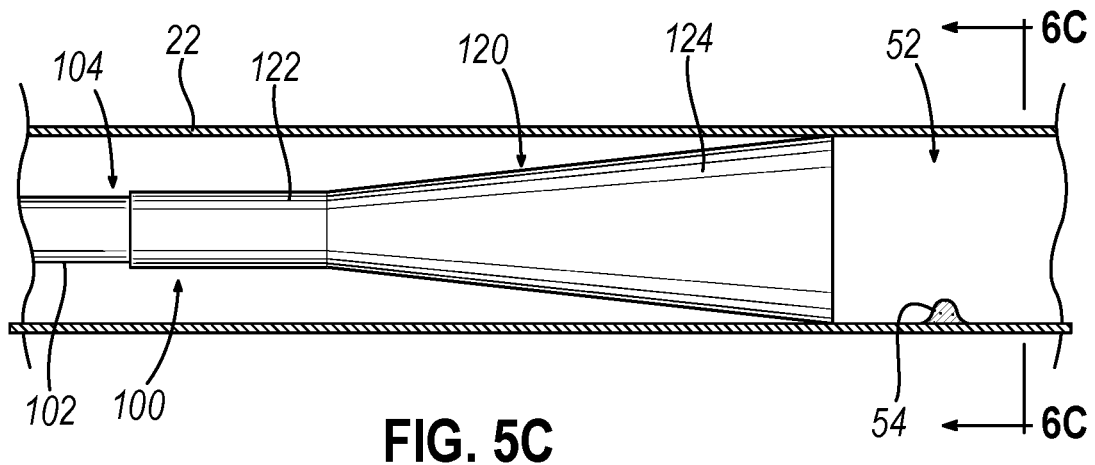
FIG. 5C depicts a cross-sectional end view of the lumen inspection device of FIG. 3A disposed in the catheter instrument of FIG. 1, with the sealing member positioned internally with in the lumen of the catheter instrument, and with the sealing member positioned proximally in relation to a particle in the lumen.
Figure 6C:
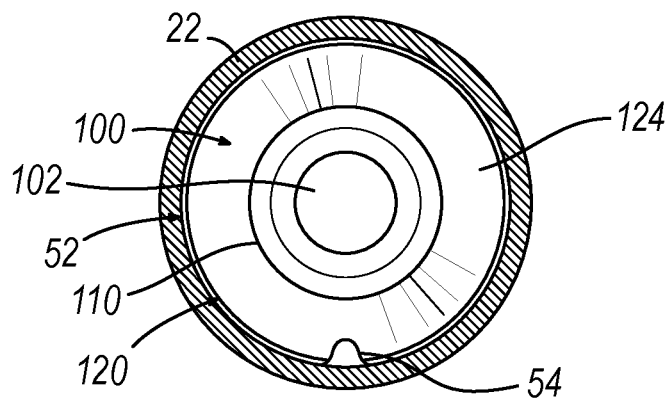
FIG. 6C depicts a cross-sectional end view of the lumen inspection device of FIG. 3A disposed in the catheter instrument of FIG. 1, taken along line 6C-6C of FIG. 5C.

At the stage shown in FIGS. 5C and 6C, sealing member (120) has reached a longitudinal position where sealing member (120) has cleared contaminant (54) and sealing member (120) is now proximal to contaminant (54). At this stage, the resilience of flared portion (124) has urged the previously-deformed part of flared portion (124) back into contact with the sidewall of lumen (52). In other words, the full circumference of flared portion (124) is now back in full contact with the sidewall of lumen (52), just like the state shown in FIG. 5A. With flared portion (124) fully contacting the sidewall of lumen (52), the pressurized fluid again builds up in the region of lumen (52) that is proximal to sealing member (120). In addition, the fluid flow rate drops back down to the zero value or nominal value, where it was during the stage shown in FIG. 5A. The operator may continue to pull lumen inspection device (100) proximally through lumen (52), with flow sensor (16) tracking the rate of fluid flow through lumen (52), until sealing member (120) ultimately exits catheter instrument (10) via port (14).

During the proximal translation of lumen inspection device (100) relative to catheter instrument (10), lumen inspection device (100) may translate at a substantially constant rate. In some versions, this is performed by a human operator manually pulling proximally on lumen inspection device via wire member (102) at a substantially constant rate of translation. In some other versions, a machine is used to pull lumen inspection device (100) proximally through catheter instrument (10) at a substantially constant rate of translation. In some variations, the rate of translation of inspection device (100) along catheter instrument (10) is variable. In some such versions, the variable rate of translation is known. Some versions of variable translation may also include proving different rates of translation of inspection device (100) along catheter instrument (10) based on the longitudinal position of inspection device (100) in catheter instrument (10). For instance, inspection device (100) may translate at a first constant rate as inspection device (100) traverses a first portion of the length of catheter instrument (10); then at a second constant rate as inspection device (100) traverses a second portion of the length of catheter instrument (10); then at a third constant rate as inspection device (100) traverses a third portion of the length of catheter instrument (10). Alternatively, any other suitable translation rates and algorithms may be used.

Figure 7:
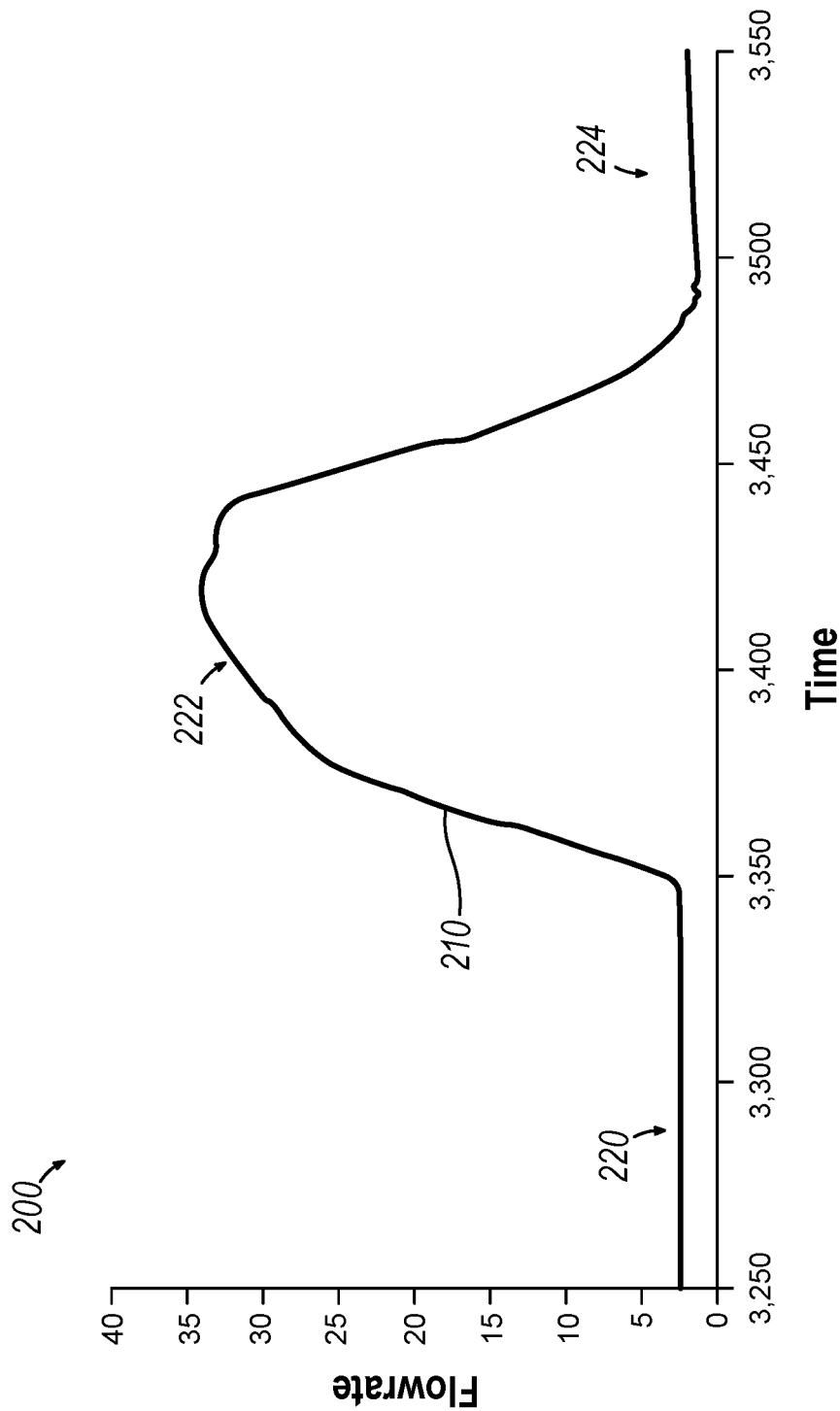
FIG. 7 shows a graph depicting an example of a plot of air flowrate as a function of time while the sealing member of the lumen inspection device of FIG. 3A traverses a lumen with a particle contained in the lumen.

FIG. 7 shows a graph (200) with a plot (210) of the fluid flow rate through lumen (52) during the stages of operation shown in FIGS. 5A-6C. The data shown by plot (210) may be provided via flow sensor (16). A first region (220) of plot (210) shows a nominal flow rate associated with the stage of operation depicted in FIGS. 5A and 6A. This nominal flow rate of first region (220) may be consistent with a baseline reading of the flow rate that is taken via flow sensor (16) when sealing member (120) initially enters lumen (52) via distal opening (50).

A second region (222) of plot (210) shows a sudden increase in flow rate associated with the stage of operation depicted in FIGS. 5B and 6B. As noted above, at this stage, contaminant (54) causes deformation of flared portion (124), thereby partially breaking the seal between sealing member (120) and the sidewall of lumen (52), thereby allowing some of the pressurized fluid to flow distally past sealing member (120). The level to which the flow rate increases may be proportional to the size of contaminant (54), such that large contaminants may create large increases in flow rate and small contaminants (54) may create small increases in flow rates. It may therefore be possible to determine the size of contaminant (54) based on the level to which the flow rate increases. In any case, flow sensor (16) may be configured to provide an alert indicating the presence of contaminant (54) when a sudden increase in flow rate is indicated by the flow rate exceeding a certain threshold value (e.g., 30 SCCM). In some such cases, increases in the flow rate that still fall below the threshold value may be deemed negligible.

A third region (224) of plot (210) shows the flow rate returning to the nominal level, consistent with the stage of operation depicted in FIGS. 5C and 6C.

In some versions, an alert feature is coupled with flow sensor (16) and is configured to alert an operator in the event that flow sensor (16) detects a sudden increase in the flow rate, such as the increase shown in second region (222) of plot (210). For instance, such an alert may include an audio alert, a visual alert, or combinations thereof. The alert may be provided in the form of a graphical and/or textual report; or may take any other suitable form. In response to receiving the alert, the operator may subject catheter instrument (10) to another cleaning process and/or other processing to try to remove contaminant (54) from lumen (52). The operator may then use lumen inspection device (100) to test catheter instrument (10) again, to see if the additional effort was successful in removing contaminant (54) from lumen (52).

As noted above, the level to which the flow rate increases during the stages represented in FIGS. 5B and 6B (and second region (222) of plot (210)) may indicate the size of contaminant (54). This size information may also be reported to the operator. The operator may tailor the response to the alert based on the reported size of contaminant (54). In some scenarios, flow sensor (160) may enable the user to define a particle size threshold for detection; and may tailor the flow rate threshold value for alerts accordingly. In addition, some versions may be configured to differentiate between contaminants (54) in lumen (52) and kinks in lumen (52) based on changes in the flow rate. In some such scenarios, a detected contaminant (54) may trigger an alert for the operator to clear the contaminant (54); while a detected kink may not trigger an alert since contaminants may present greater risks to patients (e.g., in the form of embolic debris) than kinks when an instrument such as catheter instrument (10) is subsequently used in the patient. By way of example only, a kink in lumen (52) may be distinguished from a contaminant (54) in lumen based on the rapidity of the rise or fall of the flow rate increase.

While flow sensor (16) is used to detect sudden increases in the flow rate of fluid through lumen (52) that would tend to indicate the presence of contaminants (54) in lumen (52), some other versions may provide a pressure sensor that tracks the fluid pressure level within lumen (52). Such a pressure sensor may be used in addition to, or in lieu of, flow sensor (16). Such a pressure sensor may be used to detect sudden decreases in the pressure of fluid in lumen (52), with such sudden pressure decreases indicating presence of contaminants (54) in lumen (52) as sealing member (120) traverses lumen (52).

Figure 8:
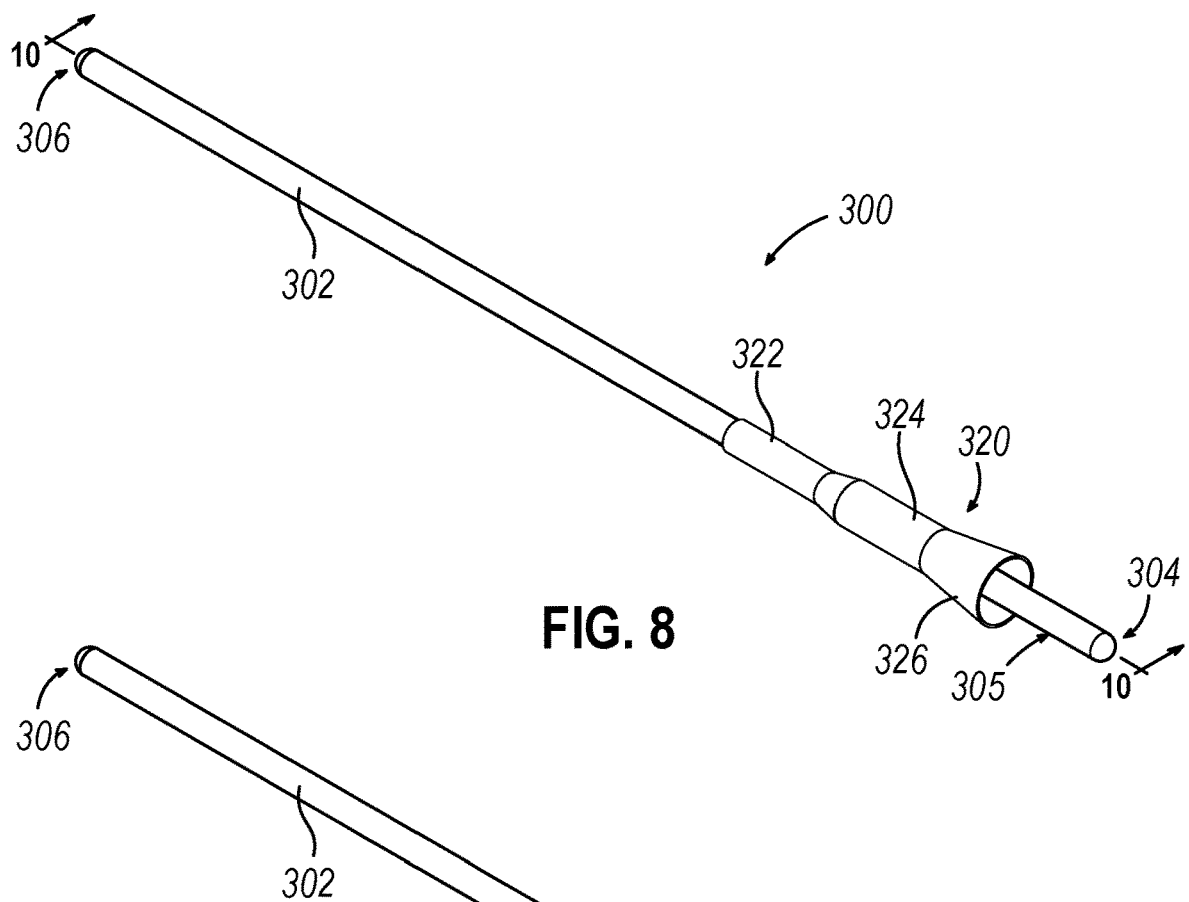
FIG. 8 depicts a perspective view of another example of a lumen inspection device.
Figure 9:
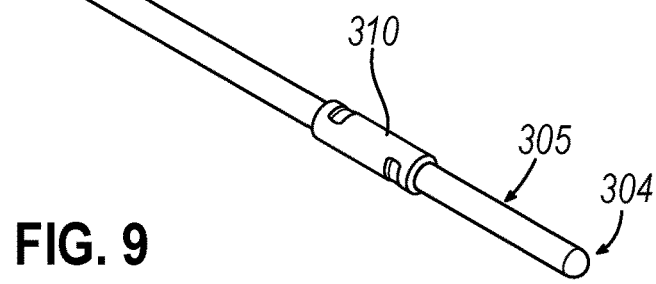
FIG. 9 depicts a perspective view of a wire member and stop member of the lumen inspection device of FIG. 8.
Figure 10:
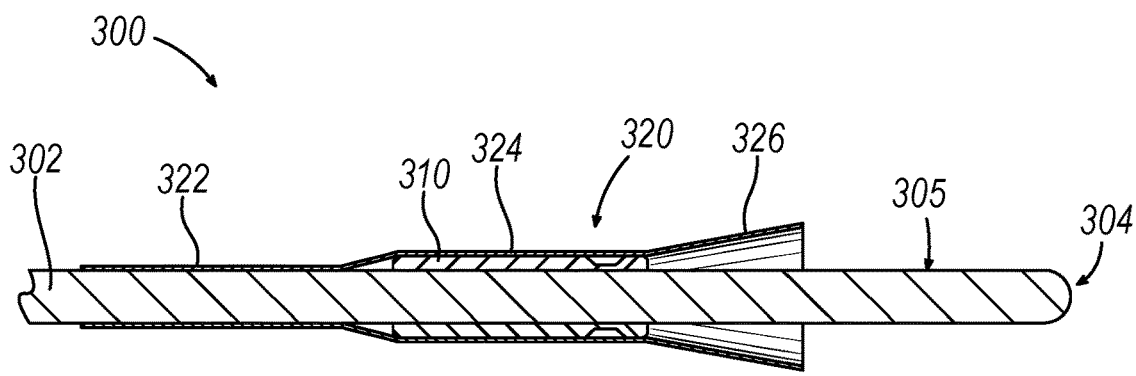
FIG. 10 depicts a cross-sectional view of the lumen inspection device of FIG. 8, taken along line 10-10 of FIG. 8.

FIGS. 8-10 show another example of a lumen inspection device (300) that may be used in the same manner as described above with respect to lumen inspection device (100). Except as otherwise described below, lumen inspection device (300) may be configured and operable like lumen inspection device (100). Lumen inspection device (300) of this example includes a wire member (302) and a sealing member (320). Wire member (302) includes a distal end (304) and a proximal end (306). A stop member (310) is fixedly secured to wire member (302), proximal to distal end (304). A distal segment (305) of wire member (302) thus extends between stop member (310) and distal end (304).

Sealing member (320) of lumen inspection device (300) includes a first sleeve portion (322), a second sleeve portion (324) extending distally from first sleeve portion (322), and a flared portion (326) extending distally from second sleeve portion (324). Sealing member (320) is formed of a polymeric material that is resiliently biased to form a tapered profile along flared portion (326). Sealing member (320) is positioned along wire member (302) such that first sleeve portion (322) extends about a corresponding portion of wire member (302); and such that second sleeve portion (324) extends about stop member (310). First sleeve portion (322) may be bonded directly to wire member (302) thermally, via an adhesive, or in any other suitable fashion. Similarly, second sleeve portion (324) may be bonded directly to stop member (310) thermally, via an adhesive, or in any other suitable fashion. While sealing member (320) provides a tapered transition between sleeve portions (322, 324) in this example, sealing member (320) may instead provide a stepped transition or any other suitable kind of transition between sleeve portions (322, 324).

Lumen inspection device (300) of this example is configured such that distal segment (305) of wire member (302) extends through flared portion (326) and extends further distally past sealing member (320). In some scenarios, after lumen inspection device (300) is used to inspect a lumen (e.g., lumen (52), as described above), it may be beneficial to use an additional tool to engage the interior of flared portion (326) to assist flared portion (326) to return to the frustoconical shape. In such scenarios, with distal segment (305) of wire member (302) extending distally past sealing member (320), distal segment (305) may assist in providing purchase or mechanical ground relative to sealing member (320) during such use of a tool to return flared portion (326) to the frustoconical shape.

While the foregoing examples are provided in the context of a contaminant (54) in lumen (52) the same process with lumen inspection device (100, 300) may be used to detect kinks, scratches, skives, bumps, and/or other surface irregularities in lumen (52). In some cases where such irregularities represent uncurable structural defects of catheter instrument (10), the detection of such irregularities may warrant disposal of catheter instrument (10) in lieu of further processing.

III. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method comprising: (a) inserting an elongate member of a lumen inspection device in a lumen of a medical instrument; (b) translating the lumen inspection device along the lumen of the medical instrument, the lumen inspection device including a sealing member, the sealing member resiliently bearing against a sidewall of the lumen as the lumen inspection device is translated along the lumen of the medical instrument; (c) activating a pressure source to pressurize a region of the lumen adjacent to the sealing member; and (d) monitoring a fluid property of the lumen during the acts of translating and activating, to thereby detect whether the sealing member deforms in response to an obstruction in the lumen.

Example 2

The method of Example 1, the elongate member comprising a wire.

Example 3

The method of Example 2, the wire comprising nitinol.

Example 4

The method of any of Examples 1 through 3, the medical instrument comprising a catheter.

Example 5

The method of Example 4, the catheter having an end effector with one or more electrodes.

Example 6

The method of Example 5, the lumen having a distal opening at the end effector.

Example 7

The method of any of Examples 1 through 6, the act of inserting comprising inserting the elongate member into a distal opening of the lumen, the distal opening being positioned at a distal end of a shaft assembly of the medical instrument.

Example 8

The method of any of Examples 1 through 7, the act of translating comprising pulling the lumen inspection device proximally through the lumen.

Example 9

The method of any of Examples 1 through 8, the act of translating comprising translating the lumen inspection device at a constant rate of translation.

Example 10

The method of any of Examples 1 through 9, the lumen inspection device being configured such that a proximal portion of the lumen inspection device extends proximally from a handle of the medical instrument during at least part of the act of translating.

Example 11

The method of Example 10, the handle including a port, the port forming a fluid tight seal around the elongate member during the act of translating.

Example 12

The method of Example 11, the act of activating including activating a pressure source to communicate pressurized fluid to the lumen via the port.

Example 13

The method of any of Examples 1 through 12, the act of activating comprising communicating pressurized air to a region of the lumen that is proximal to the sealing member.

Example 14

The method of any of Examples 1 through 13, the act of monitoring comprising monitoring a fluid flow rate through the lumen.

Example 15

The method of any of Examples 1 through 14, further comprising: (a) comparing the monitored fluid property to a baseline value; and (b) determining that the lumen contains an obstruction in response to the monitored fluid property exceeding the baseline value.

Example 16

The method of any of Examples 1 through 15, further comprising: (a) determining that an obstruction is present in the lumen based on a change in the monitored fluid property; and (b) alerting an operator in response to determining that the obstruction is present in the lumen.

Example 17

An apparatus, comprising: (a) an elongate wire having a proximal end and a distal end; (b) a stop member fixedly secured to the distal end of the elongate wire; and (c) a sealing member, the sealing member including a flared portion, the flared portion being resiliently biased to define a frustoconical shape, the sealing member having an interior region, the stop member being positioned within an interior region of the frustoconical shape, the stop member being configured to restrict distal translation of the sealing member relative to the elongate wire.

Example 18

The apparatus of Example 17, the sealing member being slidably disposed on the elongate wire.

Example 19

A kit, comprising: (a) a medical instrument having a shaft defining a lumen; (b) a lumen inspection device comprising: (i) a flexible elongate member having a distal end, and (ii) a sealing member at the distal end of the flexible elongate member, the lumen inspection device being configured to translate through the lumen, the sealing member being configured to resiliently bear against a sidewall of the lumen as the lumen inspection device translates through the lumen; (c) a pressure source operable to pressurize a region of the lumen adjacent to the sealing member as the lumen inspection device translates through the lumen; and (d) a fluid property monitor operable to monitor a fluid property of the lumen as the lumen inspection device translates through the lumen, to thereby detect whether the sealing member deforms in response to an obstruction in the lumen.

Example 20

The kit of Example 19, the medical instrument further including an end effector positioned at a distal end of the shaft, the end effector including one or more electrodes, the lumen having a distal opening at the end effector.

IV. Miscellaneous

It should be understood that any of the versions of the instruments described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those of ordinary skill in the art.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A method comprising:
   (a) inserting an elongate member of a lumen inspection device in a lumen of a medical instrument;
   (b) translating the lumen inspection device along the lumen of the medical instrument, the lumen inspection device including a sealing member, the sealing member resiliently biasing against a sidewall of the lumen as the lumen inspection device is translated along the lumen of the medical instrument, the resilient biasing of the sealing member resulting in a resilient force being applied to the sidewall of the lumen;
   (c) activating a pressure source to pressurize a region of the lumen adjacent to the sealing member; and
   (d) monitoring a fluid flow rate or a fluid pressure of the pressurized region of the lumen while translating the lumen inspection device and activating the pressure source, to thereby detect whether the sealing member deforms in response to an obstruction in the lumen.

2. The method of claim 1, the elongate member comprising a wire.

3. The method of claim 2, the wire comprising nitinol.

4. The method of claim 1, the medical instrument comprising a catheter.

5. The method of claim 4, the catheter having an end effector with one or more electrodes.

6. The method of claim 5, the lumen having a distal opening at the end effector.

7. The method of claim 1, the act of inserting comprising inserting the elongate member into a distal opening of the lumen, the distal opening being positioned at a distal end of a shaft assembly of the medical instrument.

8. The method of claim 1, the act of translating comprising pulling the lumen inspection device proximally through the lumen.

9. The method of claim 1, the act of translating comprising translating the lumen inspection device at a constant rate of translation.

10. The method of claim 1, the lumen inspection device being configured such that a proximal portion of the lumen inspection device extends proximally from a handle of the medical instrument during at least part of the act of translating.

11. The method of claim 10, the handle including a port, the port forming a fluid tight seal around the elongate member during the act of translating.

12. The method of claim 11, the act of activating including activating a pressure source to communicate pressurized fluid to the lumen via the port.

13. The method of claim 1, the act of activating comprising communicating pressurized air to a region of the lumen that is proximal to the sealing member.

14. The method of claim 1, the act of monitoring comprising monitoring a fluid flow rate through the lumen.

15. The method of claim 1, further comprising:
   (a) comparing the monitored fluid flow rate or fluid pressure to a baseline value; and
   (b) determining that the lumen contains an obstruction in response to the monitored fluid flow rate or fluid pressure exceeding the baseline value.

16. The method of claim 1, further comprising:
   (a) determining that an obstruction is present in the lumen based on a change in the monitored fluid flow rate or fluid pressure; and
   (b) alerting an operator in response to determining that the obstruction is present in the lumen.

17. An apparatus, comprising:
   (a) an elongate wire having a proximal end and a distal end;
   (b) a stop member fixedly secured to the distal end of the elongate wire; and
   (c) a sealing member, the sealing member including a flared portion, the flared portion being resiliently biased to define a frustoconical shape, the sealing member having an interior region, the stop member being positioned within an interior region of the frustoconical shape, the stop member being configured to restrict distal translation of the sealing member relative to the elongate wire, the flared portion being configured to deflect inwardly to thus break a fluid seal between the sealing member and a lumen upon encountering a contaminant between the sealing member and the lumen.

18. The apparatus of claim 17, the sealing member being slidably disposed on the elongate wire.

19. A kit, comprising:
   (a) a medical instrument having a shaft defining a lumen;
   (b) a lumen inspection device comprising:
      (i) a flexible elongate member having a distal end, and
      (ii) a sealing member at the distal end of the flexible elongate member, the lumen inspection device being configured to translate through the lumen, the sealing member having a resilient bias with a flared configuration such that the sealing member is configured to resiliently bias against a sidewall of the lumen as the lumen inspection device translates through the lumen;
   (c) a pressure source operable to pressurize a region of the lumen adjacent to the sealing member as the lumen inspection device translates through the lumen; and
   (d) a fluid parameter monitor operable to monitor a fluid flow rate or a fluid pressure of fluid in the lumen as the lumen inspection device translates through the lumen, to thereby detect whether the sealing member deforms in response to an obstruction in the lumen.

20. The kit of claim 19, the medical instrument further including an end effector positioned at a distal end of the shaft, the end effector including one or more electrodes, the lumen having a distal opening at the end effector.

* * * * *